(12) United States Patent
Lee et al.

(10) Patent No.: US 10,932,904 B2
(45) Date of Patent: Mar. 2, 2021

(54) ARTIFICIAL HEART VALVE

(71) Applicant: Shanghai Joy Medical Devices Co., Ltd., Shanghai (CN)

(72) Inventors: Shouyan Lee, Rancho Santa Margarita, CA (US); Hongxia Nan, Shanghai (CN)

(73) Assignee: SHANGHAI JOY MEDICAL DEVICES CO., LTD, Shanghai (CN)

( * ) Notice: Subject to any disclaimer, the term of this patent is extended or adjusted under 35 U.S.C. 154(b) by 83 days.

(21) Appl. No.: 16/467,054

(22) PCT Filed: Apr. 7, 2017

(86) PCT No.: PCT/CN2017/079777
§ 371 (c)(1),
(2) Date: Jun. 6, 2019

(87) PCT Pub. No.: WO2018/184225
PCT Pub. Date: Oct. 11, 2018

(65) Prior Publication Data
US 2019/0388221 A1   Dec. 26, 2019

(51) Int. Cl.
*A61F 2/24* (2006.01)
*A61F 2/915* (2013.01)
(Continued)

(52) U.S. Cl.
CPC .......... *A61F 2/2418* (2013.01); *A61F 2/2412* (2013.01); *A61F 2/2436* (2013.01);
(Continued)

(58) Field of Classification Search
CPC ..... A61F 2/2418; A61F 2/2412; A61F 2/2436
See application file for complete search history.

(56) References Cited

U.S. PATENT DOCUMENTS

| 2014/0012371 A1 | 1/2014 | Li |
| 2017/0000603 A1* | 1/2017 | Conklin ................ A61F 2/2409 |

FOREIGN PATENT DOCUMENTS

| CN | 102036622 | 4/2011 |
| CN | 2011800233449 | 11/2011 |

(Continued)

*Primary Examiner* — Suba Ganesan
(74) *Attorney, Agent, or Firm* — Treasure IP Group, LLC

(57) ABSTRACT

A device for treating regurgitation of a tricuspid valve (4). The device comprises a tricuspid valve plug (21) capable of compressing and expanding and a tricuspid valve plug fixing device used for anchoring the tricuspid valve plug (21) to an orifice of the tricuspid valve (4). The tricuspid valve plug (21) is provided with an inflow end (42, 52) and an opposite outflow end (47, 57), and a prosthetic valve (50, 70) capable of being opened and closed is disposed in the tricuspid valve plug (21). When the tricuspid valve (4) is closed, the prosthetic valve (50, 70) is automatically closed, and when the tricuspid valve (4) is opened, the prosthetic valve (50, 70) is automatically opened. The device for treating regurgitation of a tricuspid valve (4) and the implantation method therefor help to treat regurgitation of a tricuspid valve and do not block the flow of blood in a heart, and the device can be recycled, has the characteristics of high operationality and high safety in minimally-invasive repair, and has high clinical value.

19 Claims, 9 Drawing Sheets

(51) Int. Cl.
*B33Y 80/00* (2015.01)
*A61F 2/91* (2013.01)

(52) U.S. Cl.
CPC ............ *A61F 2/915* (2013.01); *A61F 2/2415* (2013.01); *A61F 2/91* (2013.01); *A61F 2002/9155* (2013.01); *A61F 2210/0014* (2013.01); *A61F 2220/0008* (2013.01); *A61F 2220/0075* (2013.01); *A61F 2250/001* (2013.01); *A61F 2250/0048* (2013.01); *A61F 2250/0082* (2013.01); *B33Y 80/00* (2014.12)

(56) References Cited

FOREIGN PATENT DOCUMENTS

| | | |
|---|---|---|
| CN | 201180036365.4 | 12/2011 |
| CN | 102764169 | 11/2012 |
| CN | 104507417 | 4/2015 |
| CN | 105125322 | 12/2015 |
| WO | 2011143238 | 11/2011 |
| WO | 2011147849 | 12/2011 |

\* cited by examiner

US 10,932,904 B2

ARTIFICIAL HEART VALVE

CROSS REFERENCE TO RELATED APPLICATION

This application is a national stage application of PCT/CN2017/079777, filed on Apr. 7, 2017. The international application is incorporated herein by reference in its entirety.

TECHNICAL FIELD

The present invention pertains to a prosthetic valve, which can be implanted into the pulmonary and/or tricuspid position in a human body to replace the diseased pulmonary or tricuspid valve.

BACKGROUND OF THE INVENTION

A human heart has four pumping chambers, that is, atrium sinistrum, atrium dextrum, ventriculus sinister and ventriculus dexter. The atriums receive blood from veins and pump it into the ventricles, and the ventricles discharge the blood to arteries. Atrium sinistrum, atrium dextrum, ventriculus sinister and ventriculus dexter individually have a valve, and the four valves control the blood stream that circulates through the human body. The mitral valve, located on the left part of heart, connects the atrium sinistrum with the ventriculus sinister, and the aortic valve connects the ventriculus sinister with the aorta. The two valves deliver oxygenated blood from the lungs into the aorta for distribution through the body. The tricuspid connecting the atrium dextrum and ventriculus dexter and the pulmonary valve connecting the ventriculus dexter and the pulmonary artery are located on the right part of heart, and together they deliver deoxygenated blood from the body to the lungs. The tricuspid is defined by fibrous rings of collagen, each of which is referred to as a valve annulus, and form part of the fiber skeleton of heart, and the valve annulus provides peripheral attachment for the three cuspides or leaflets of tricuspid. A pulmonary valve generally has three leaflets.

Pulmonary valve stenosis generally refers to the stenosis of a pulmonary valve or the combination of a pulmonary valve and the right ventricular outflow tract, and it may exist isolately and may also be one of the lesions of other complex congenital heart diseases (such as Tetralogy of Fallot). The morbidity from pulmonary stenosis accounts for 10%-20% of the total cases of congenital heart diseases. Depending on different sites of stenosis, pulmonary valve stenosis may be classified as pulmonary valve stenosis, infundibular stenosis, and main pulmonary artery and pulmonary branch stenosis, wherein pulmonary valve stenosis is the most common. The surgery treatment for pulmonary stenosis should be determined according to different lesions, and particularly include (1) pulmonary valve commissurotomy, (2) infundibulum hypertrophic excision, (3) surgical treatment of supravalvular pulmonary stenosis, and (4) surgical repair of pulmonary valve. However, the patches that are used in the above surgical treatments cannot conform to growth of the human body, and easily generate restenosis or valve lesions, and the condition will be increasingly severe with age.

Among right ventricular outflow tract (RVOT) reorganization surgeries for congenital heart diseases, regurgitation of the pulmonary artery is a common postoperative complication, and is nearly inevitable. In the last few decades, along with the developments in heart surgery, increasing numbers of patients having complex congenital heart diseases have lived through childhood and survived to adolescence or adulthood, and thus regurgitation of the pulmonary artery has become an increasingly problematic common disease. Originally, regurgitation of the pulmonary artery valve was considered to be a relatively benign condition tolerable, but recently the patho-physiology of and the significance of further treatment of pulmonary regurgitation got the attention of cardiovascular physicians. Furthermore, the emerging of pulmonary restenosis may probably further aggravate pulmonary regurgitation.

Besides surgical expansion of pulmonary valves/arteries, current transcatheter treatment comprises intervention modes of valve implant or balloon expansion. Transcatheter valve implant only serves as remedy for pulmonary regurgitation from the surgery and requires a secondary procedure, and the balloon expansion may also result in the complication of pulmonary regurgitation. In addition, because the patients of congenital heart diseases are mostly infants and youngsters, prosthetic valves cannot adapt for the growth of the patients, and thus have limited functionality.

Surgery has a remarkable curative effect for treating the patients that undergo RVOT surgery for the first time, but surgery for the second time increases risks of dissociation, hemorrhage and hemostasis, and complications. That is because, although the existing valves can secure themselves to the blood vessel inner wall by the radial supporting force of the stent, most of the positions to secure the stent have undergone surgical treatment, such as the valve annulus was cut during the surgery, so the elasticity and the shape of the blood vessel may no longer be suitable for conventional replacement of a stented valve so that the valve stent is prone to migration.

The existing prosthetic valve implanting techniques also include using a planar (perpendicular to a flow direction through the valve) sewing ring to suture the prosthetic valve to protogenic valve annulus. However, planar sewing rings cannot adapt to new anatomical structures correctly, and have a risk of thrombosis and stenosis.

The prior art that is used to solve the above problems is to conduct redo-surgery or replace the valve by transcatheter delivery. Both of the two methods require another procedure and will certainly cause the complication of pulmonary regurgitation, thereby affecting the function of right ventriculus. If not used for the first time, the transcatheter valve requires another procedure, and the patient may not go to a hospital until the ventriculus dexter dysfunction occurs and at that time the function restoration of ventriculus dexter may be too late.

The PCT patent for invention that has entered the Chinese national phase "PROSTHETIC HEART VALVE" (CN 201180023344.9) discloses a prosthetic valve, comprising an inflow end and an opposing outflow end; a plurality of valve leaflets; a collapsible, self-expandable frame assembly configured to support the valve leaflets and defining a plurality of commissure portions; and a sewing ring portion configured to secure the valve to a surrounding lumen, wherein the plurality of commissure portions are configured to move independently of the sewing ring when the valve is so secured.

In the patent, the self-expandable frame assembly is provided with only one base sewing ring, and thus has a relatively low height, which is inconvenient for being secured into a human heart.

The PCT patent for invention that has entered the Chinese national phase "PROSTHETIC HEART VALVE AND TRANSCATHETER DELIVERED ENDOPROSTHESIS COMPRISING A PROSTHETIC HEART VALVE AND A STENT" (CN 201180036365.4) discloses a prosthetic valve, comprising at least two, preferably three, leaflets, which consist of a natural and/or synthetic material and have a first opened position for opening the heart chamber and a second closed position for closing the heart chamber, the leaflets being able to switch between their first and second position in response to the blood flow through the heart; a leaflet support portion, consisting of biological and/or synthetic material for mounting of the prosthetic heart valve to a stent; and a bendable transition area which forms a junction between the leaflets and the leaflet support portion, the bendable transition area progressing essentially in a U-shaped manner similar to a cusp shape of a natural aortic or pulmonary heart valve for reducing tissue stresses during opening and closing motion of the leaflets.

In the patent, the structure of the stent is complicated, and the suturing structure of the valve leaflets is complicated, both of which result in a high cost for manufacturing the prosthetic valve.

Tricuspid regurgitation (TR) is also a common heart disease, and functional tricuspid regurgitation can be fatal, and often associated with left heart diseases. Generally tricuspid regurgitation is not treated alone surgically, but often performed during surgery to repair left heart lesions. Severe tricuspid regurgitation will result in low cardiac output and circulatory congestion, and usually the prognosis is poor. Literature exhibits that moderate and severe tricuspid regurgitations are closely related to increased mortality and morbidity rates.

Besides surgical treatment of tricuspid regurgitation, minimally invasive repair includes valve annuloplasty and a tricuspid plug, both of these methods are presently in the research stage. In view of the risk-benefit ratio of secondary surgery treatment of tricuspid regurgitation or postoperative degeneration of prosthetic tricuspid valve, and the problem that the existing tricuspid plugs may cause stenosis during diastole, a more effective and less invasive method of treating tricuspid regurgitation is desired.

SUMMARY OF THE INVENTION

In view of the problems of the prior art, the present disclosure provides a prosthetic valve, which is suitable for both pulmonary and tricuspid positions. The prosthetic valve is designed with foldable joints on an internal stent to allow further expansion, and the foldable joints are unfolded when the prosthetic valve is expanded after initial implant, therefore adapting for the patient growth.

To achieve the above objectives, the technical solutions of the present disclosure are realized as follows:

a prosthetic valve, comprising a tubular frame, wherein the frame is of a lattice structure that can be radially expanded and deformed, wherein, several U-shaped protrusions are evenly arranged on the frame at a downstream end relative to a blood stream direction, wherein a U-shaped recession is provided between every two adjacent protrusions, one or more foldable joints are provided on edge(s) of each of the recessions such that the protrusions and the recessions are stretched when the prosthetic valve is expanded at the initial implant, and the foldable joints are unfolded when the prosthetic valve is expanded after the initial implant.

Optionally, the prosthetic valve has three protrusions and three recessions, and three valve leaflets are attached at the protrusions and the recessions, such that the valve leaflets are able to open and close in the blood stream; a covering membrane is provided on the lattice structure of the frame, and the valve leaflets are sutured on the covering membrane such that sutured portions are hermetically joined to the covering membrane, and suturing thread is sutured on the frame or not.

Optionally, the protrusions and the recessions are formed by same smooth arcuate edge.

Optionally, 1-3 foldable joints in the shape of pointed tips are provided, and the tips of the foldable joints point axially to downstream or upstream of a blood stream.

Optionally, the recession comprises a combination of two smooth arcuate edges, and the arcuate edges are smoothly connected to the protrusions adjacent to the recessions, and bottom ends of the arcuate edges are connected to the lattice structure of the frame.

Optionally, 1-3 foldable joints are provided at each recession wherein at least 1 of the foldable joints is provided between the bottom ends of the two smooth arcuate edges, 1 foldable joint is provided on the smooth arcuate edge or not.

Optionally, rhombic meshes are provided in the lattice structure of the frame, U-shaped process slots are provided at intersections of net wires, to facilitate deformation of the net elements when the tubular frame is radially expanded, and the intersections of the net elements are of an H shape or an X shape. The H and X shape elements are shown in FIG. 8

Optionally, two or more layers of the rhombic meshes are provided, and are axially distributed along the frame, and the mesh array extend downstream to interior of the protrusions in the blood stream direction.

Optionally, the valve leaflets are sutured along edges of the protrusions and the recessions, wrinkles of the valve leaflets corresponding to the foldable joints are preserved and can be expanded and deformed when the prosthetic valve is expanded again; and wrinkles of the covering layer corresponding to the foldable joints are preserved and can be expanded and deformed when the prosthetic valve is expanded again.

Optionally, the covering membrane is provided on an inner surface, or on an outer surface, or on both of an inner surface and an outer surface, of the lattice structure of the frame.

Optionally, the covering membrane on the outer surface of the frame comprises an upper covering membrane and a lower covering membrane, the upper covering membrane wraps the protrusions and part of the frame, the lower covering membrane wraps the remaining part of the frame. The upper and the lower covering membranes are made of different materials or the same material, and are sutured together along a periphery of the frame.

Optionally, the frame and the protrusions are manufactured integrally, by laser cutting, wire braiding/weaving or 3D printing.

Optionally, the frame and its protrusions are compressed into a slim tubular shape before the prosthetic valve is radially expanded and deformed, and are expanded and deformed by a force being applied from the interior of the slim tube. Or the frame and its protrusions are manufactured by using a shape memory functional material to realize self-expansion.

Optionally, a guide loop is provided on an arch portion of each protrusion, and the guide loop is formed at the arch portion of the protrusion; or several U-shaped or V-shaped guides on the frame are provided at an upstream end relative to the blood stream direction, the guides extend out of the frame, and the guides and the frame are manufactured integrally.

Optionally, a U-shaped or V-shaped reinforcement is connected to two edges of a corresponding recession, the protruding direction of the reinforcements is the same as the arch direction of the protrusions, and the two bottom ends of each reinforcement are respectively connected to the two edges of the corresponding recession.

Optionally, a guide loop is provided on the protruding portion of each reinforcement, and the guide loop is formed at the protruding portion of the reinforcement.

Optionally, an arch portion of each protrusion is connected to a lower fixing strut, and the lower fixing struts are convergently connected to a lower circular base; several upper fixing struts on the frame are connected to the upstream end relative to the blood stream direction, and the upper fixing struts are convergently connected to an upper circular base; and width of either the upper fixing struts or the lower fixing strut is greater than width of the net wires of the frame.

Optionally, the upper circular base and the lower circular base form guiding elements, to connect to a positioning device for the prosthetic valve.

Optionally, a U-shaped or V-shaped reinforcement is connected to two edges of a corresponding recession, and the protruding direction of the reinforcements is the same as the arch direction of the protrusions, and a protruding portion of the reinforcements is connected to the lower circular base.

Optionally, the prosthetic valve is expanded for the first time during the implantation, and the prosthetic valve is also expandable after implant.

The prosthetic valve in the present disclosure has the following advantages:

The prosthetic valve of the present disclosure is suitable for surgical implantation, i.e., implanting through open heart surgery, is secured to the heart by suturing or anchoring, for example, secured to the pulmonary artery wall or on the tricuspid position, to effectively prevent pulmonary regurgitation or tricuspid regurgitation.

The prosthetic valve of the present disclosure can be expanded in diameter multiple times to adapt for the growth of the patient, which avoids the surgical procedures in the prior art that requires replacement of the prosthetic valve and alleviates the complication from redo surgery.

The prosthetic valve of the present disclosure is also suitable for implant through transcatheter delivery, so that the valve can be expanded radially to be secured at the implant location. The procedure does not require open heart surgery so it is suitable for high risk patients.

The prosthetic valve of the present disclosure can fit either the pulmonary or the tricuspid valve position.

The prosthetic valve of the present disclosure is retrievable during implant in the corresponding valve position; in the case of less optimal positioning, or residual regurgitation after positioning, it may optionally be withdrawn from the implant location.

Compared with the prior art, the prosthetic valve of the present disclosure has the characteristics of a simple structure and low manufacturing cost.

Figure 1:
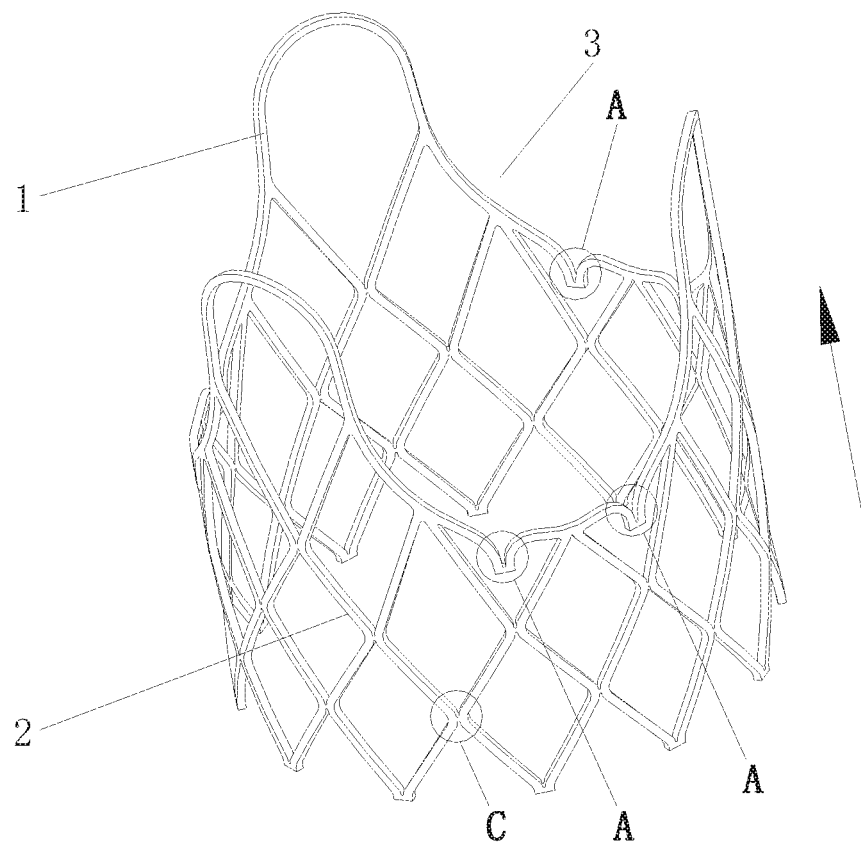
FIG. 1 is the perspective view of the stent of the prosthetic valve of Embodiment 1 in the present disclosure.

In the drawings: 1. protrusions; 2. frame; 3. recessions; 4. inner covering membrane; 4-1. suturing reference; 5. outer covering layer; 5-1. suturing line; 5-2. suturing line; 5-3. lower covering membrane; 5-4. upper covering membrane; 6. valve leaflets; 7. guides; 8. reinforcements; 9. blood vessel; 10. suturing thread.

A. foldable joint; B. foldable joint; C. X-shaped connection; D. H-shaped connection. 11. protrusion; 12. frame; 13. recession; 14. lower fixing strut; 15. upper fixing strut; 16. lower fixing base; 17. upper fixing base; 18. reinforcement.

DETAILED DESCRIPTION

The embodiments of the present invention will be further described in detail below with reference to the accompanying drawings.

Embodiment 1

FIG. 1 shows one of the embodiments of the present disclosure. In the present embodiment, the prosthetic valve that is intended for the pulmonary and tricuspid implant comprises a tubular frame 2. The frame 2 is of a lattice structure, and can be radially expanded and deformed. Three U-shaped protrusions 1 on the frame 2 are evenly arranged at the downstream end relative to blood stream direction. U-shaped recession 3 is provided between every two adjacent protrusions 1. Several foldable joints are provided on each edge of the recessions 3, such as the foldable joints A shown in FIG. 1. The protrusions 1 and the recessions 3 are stretched when the prosthetic valve is expanded during implant, and the foldable joints A are unfolded when the prosthetic valve is further expanded after implant.

The blood stream direction is indicated by the arrow in FIG. 1. The numbers of the protrusions 1 and the recessions 3 are preferably three, and the numbers may be increased according to design requirements, for example, increased to six or nine.

The purpose of the foldable joints A is to provide room for future expansion after the initial expansion of the prosthetic valve during implant. When the prosthetic valve is expanded during implant, the foldable joints A are still in the folded state, or are unfolded at a smaller scale. After the patient is implanted with the prosthetic valve, as the patient grows, the prosthetic valve may be further expanded, so as to adapt for the growth of the patient. Further expansion may be once or several times, but generally does not exceed twice.

Because the structures of the protrusions 1 and the recessions 3 on the frame 2 are all U-shaped, which has a wide bottom edge, the protrusions 1 and the recessions 3 can be stretched more easily than the foldable joints A that are of smaller size; this structure is substantially different from the V-shaped protrusions and recessions that are commonly used in the prior art. If the protrusions 1 and the recessions 3 are V-shaped, the side edges of the protrusions and the recessions will, during initial expansion, make the small foldable joints unfold together, so future expansion may be limited.

Figure 3:
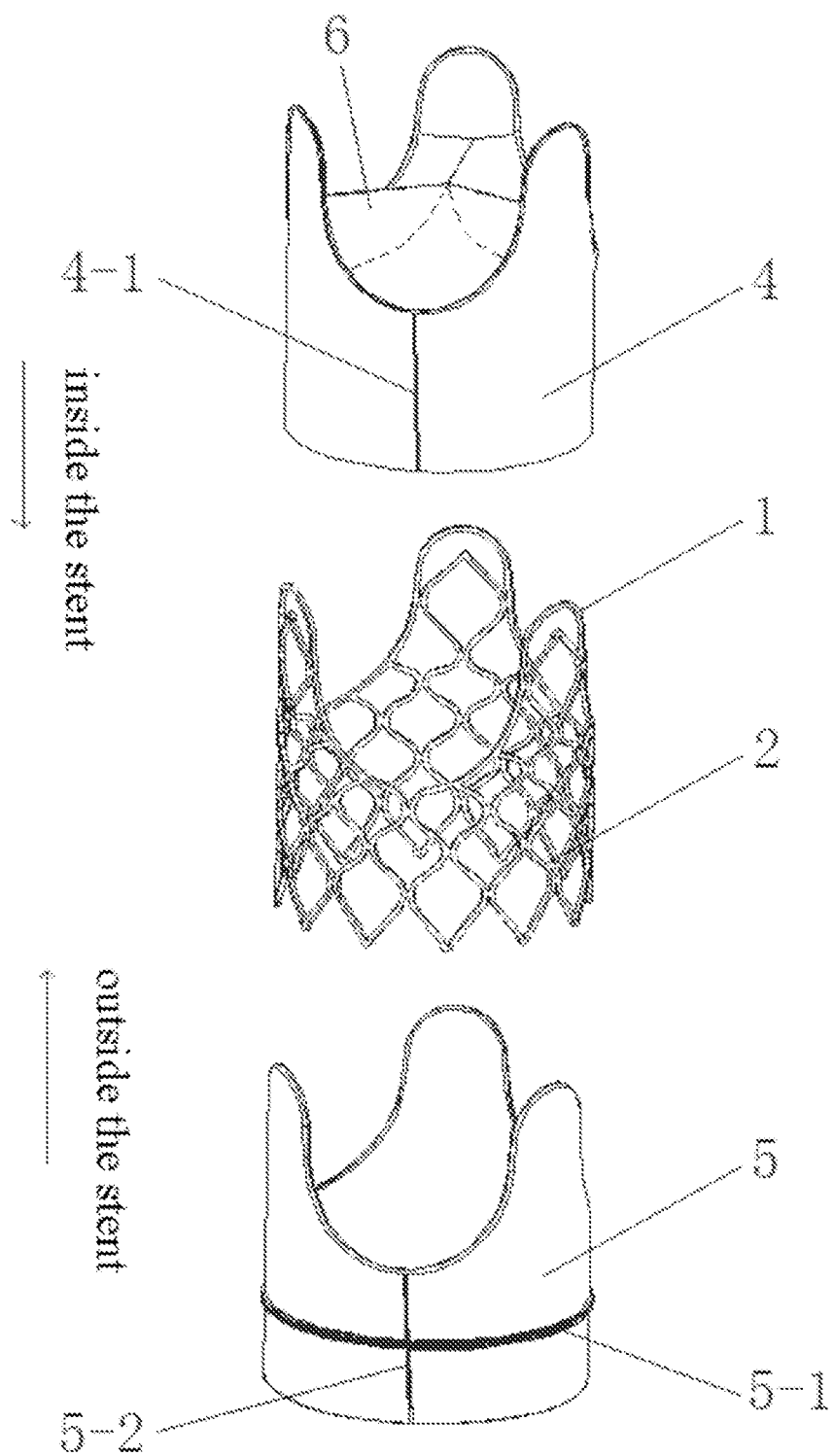
FIG. 3 is the exploded view of the prosthetic valve of the present disclosure.
Figure 8:
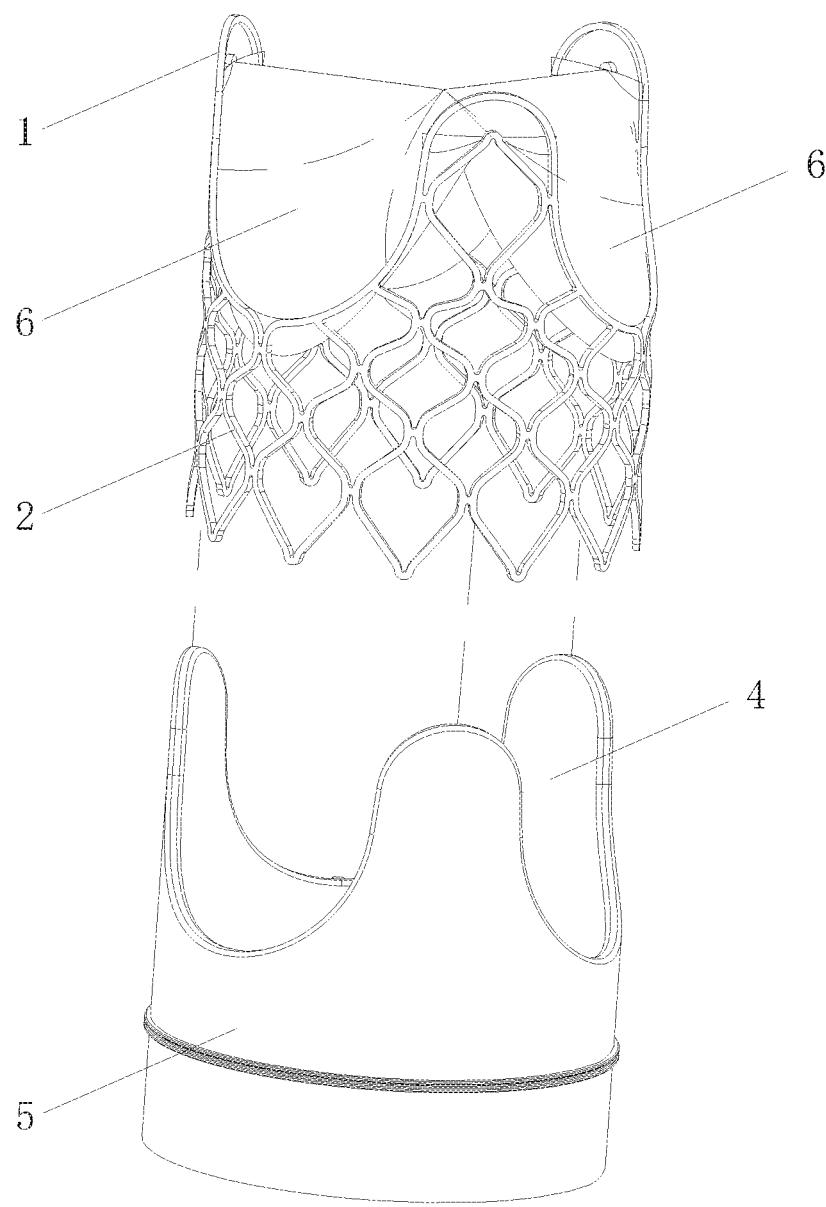
FIG. 8 is a diagram of the positional relationship between the stent and the valve leaflets attachment of the prosthetic valve in the present disclosure.

As shown by FIGS. 3 and 8, three valve leaflets 6 are attached at the protrusions 1 and the recessions 3 so that the valve leaflets 6 are able to open and close in the blood stream. A covering membrane is provided on the lattice structure of the frame 2. The valve leaflets 6 are sutured on the covering membrane, with sutured portions hermetically engaged to the covering membrane. If the valve leaflets 6 are directly sutured on an internal stent, each of the suturing points forms a stress concentration; if they are sutured on the covering membrane, the stress will be more evenly distributed. The suturing thread may optionally be sutured through the frame 2 or not.

The valve leaflets 6 may be designed with various shapes, such as half-moon shape, elliptical shape, U shape or approximately egg shape. The material of the valve leaflets 6 may employ animal (preferably pig) valves, pig or cattle pericardium materials, biological tissue materials, polymer materials or tissue engineering materials.

As shown by FIG. 1, the protrusions 1 and the recessions 3 are of a smooth arcuate edge.

In the present embodiment, 1-3 foldable joints A in a shape of pointed tips are provided, and the tips of the foldable joints A point axially to downstream or upstream of blood stream direction. When the prosthetic valve is expanded after implant, the foldable joints A may be unfolded.

Rhombic meshes are provided in the lattice structure of the frame 2. U-shaped process joints are formed at intersections of net wires to facilitate deformation of the meshes when the tubular frame is radially expanded, and the intersections of the net wires are of an H shape or an X shape, such as the X-shaped connection C shown in FIG. 1. The shape of the meshes is not limited rhombic; for example, it may be set to be hexagonal meshes, as long as the shape allows compressing and expanding.

As shown by FIG. 1, at least an upper layer and a lower layer of the rhombic meshes are axially distributed along the frame, and the meshes extend until the three U-shaped protrusions 1 in the direction of blood stream. This structure increases the structural strength of the protrusions 1 and allows adjustment of elasticity of the protrusions 1.

The valve leaflets 6 are sutured in reference to edges of the protrusions 1 and the recessions 3, wrinkles corresponding to the foldable joints A on the valve leaflets are preserved, and can be stretched and deformed when the prosthetic valve is expanded after implant. The design of the wrinkles is required to form the seal, and to prevent perivavular leak.

The covering membrane also has wrinkles corresponding to the foldable joints A, and can be stretched and distorted when the prosthetic valve is expanded after implant. The design of the wrinkles is required to form a seal, and to prevent perivavular leak.

Figure 4:
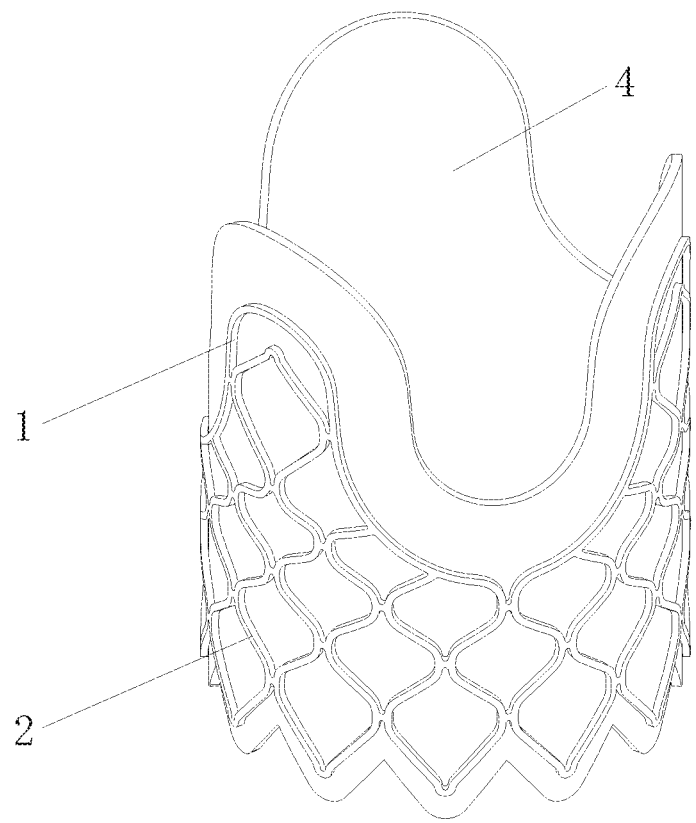
FIG. 4 is the assembly view of the inner covering membrane and the stent of the prosthetic valve in the present disclosure.
Figure 5:
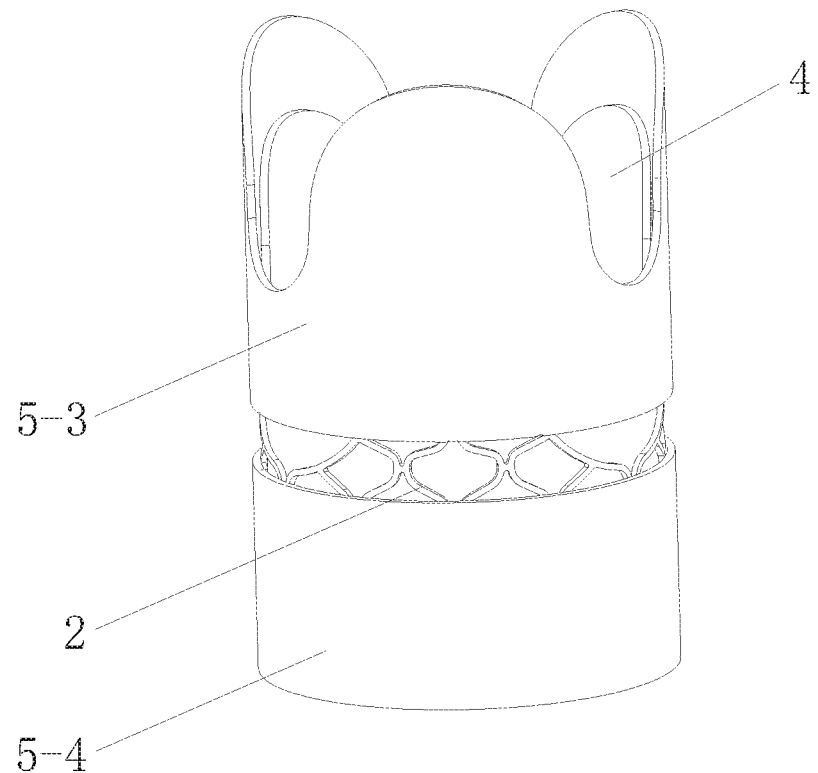
FIG. 5 is the assembly view of the inner covering membrane, the outer covering membrane and the stent of the prosthetic valve in the present disclosure.
Figure 6:
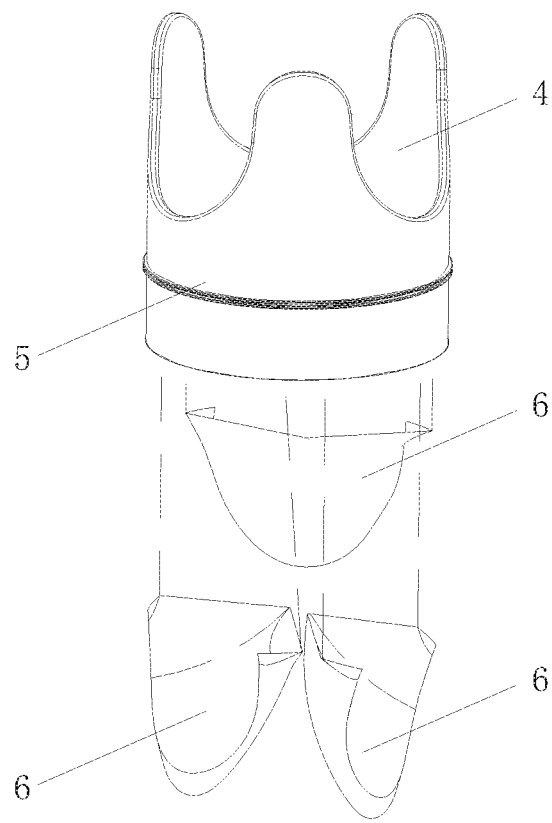
FIG. 6 is the assembly view of the covering membranes and the valve leaflets of the prosthetic valve in the present disclosure.
Figure 7:
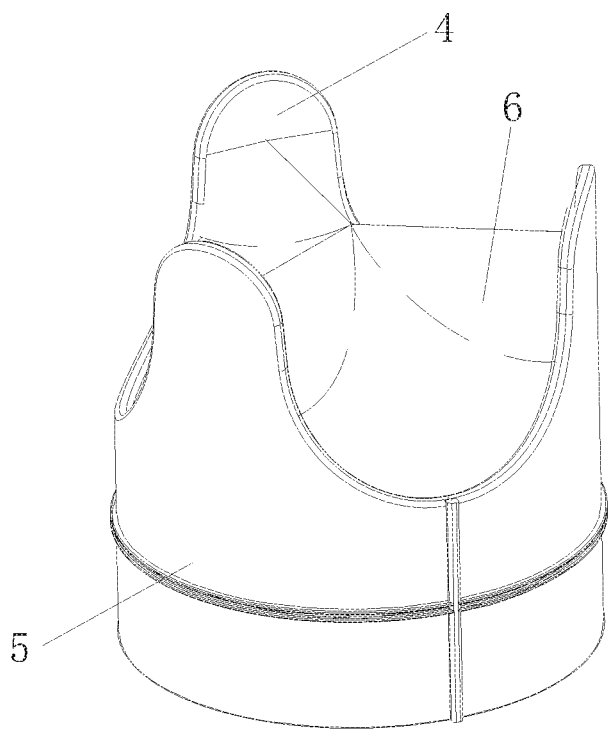
FIG. 7 is the perspective view of the final assembly of the prosthetic valve in the present disclosure.

As shown by FIGS. 3, 4 and 5, covering membranes are provided on both of the inner surface and the outer surface of the lattice structure of the frame 2, that is, the inner covering membrane 4 and the outer covering membrane 5 in the figures. The inner covering membrane 4 and the outer covering membrane 5 are required to be sutured together at the both ends of the frame.

The inner covering membrane 4 on the inner surface is required to be sutured in the axial direction of the frame 2 (the suturing edge 4-1).

The outer covering membrane 5 on the outer surface comprises an upper part and a lower part, the upper part 5-3 wraps the three U-shaped protrusions 1 and part of the frame body of the frame 2; the lower part 5-4 wraps the remaining part of the frame body of the frame 2. The upper and the lower coverings can be made of different materials or of the same material. They are firstly individually sutured in the axial direction of the frame 2 (the suturing edge 5-2), and then sutured together along the periphery of the frame 2 (the suturing edge 5-1). The upper part 5-3 is made of pericardium materials, such as porcine or bovine pericardium material, which have the characteristics of a smooth surface and is resistant to thrombus formation. The material of the lower covering 5-4 is not specially limited, and it may employ the material the same as that of 5-3. The material of the covering membrane may also be selected from any of polyethylene materials, artificial tissue materials and polyurethane materials.

The "artificial tissue materials" include tissues that are manufactured by tissue engineering in a laboratory, such as the combination of extracellular matrixes, cells and biologically active molecules as designed. They can prevent the calcification problems of natural tissue materials, which results in undesirable structural deterioration of artificial heart valves. The "artificial tissue materials" may employ tissue originated from kangaroo, ostrich, whale or any other suitable heterograft or homograft of any reasonable size. The "artificial tissue materials" also include connective tissue proteins that are employed as the supporting frames of tissue materials (that is, collagen and elastin). In order to strengthen the tissue protein compound, a chemical fixation process can be employed to link proteins.

The frame 2 and the three U-shaped protrusions 1 are manufactured in one process, and are manufactured by laser cutting, wire braiding/weaving or 3D printing. The frame 2 and the three U-shaped protrusions 1 are optionally manufactured by using elastic metal materials, such as stainless steel, and may also be manufactured by using shape memory alloy materials, such as nickel titanium alloy.

The frame 2 and the three U-shaped protrusions 1 were compressed into a slim tube shape before the prosthetic valve is radially expanded and deformed, and a force is applied from the interior of the tube shape to make the frame 2 and the three U-shaped protrusions 1 expand and deform.

The implanting method and the implanting instruments may refer to the implant procedures in the prior art.

If the prosthetic valve is implanted by surgery, the prosthetic valve is required to be expanded to a suitable size before the suturing to the implant position. If the prosthetic valve is implanted by transcatheter delivering, the prosthetic valve is expanded to a suitable size after it has been delivered to the pulmonary valve or the tricuspid position.

Figure 9:
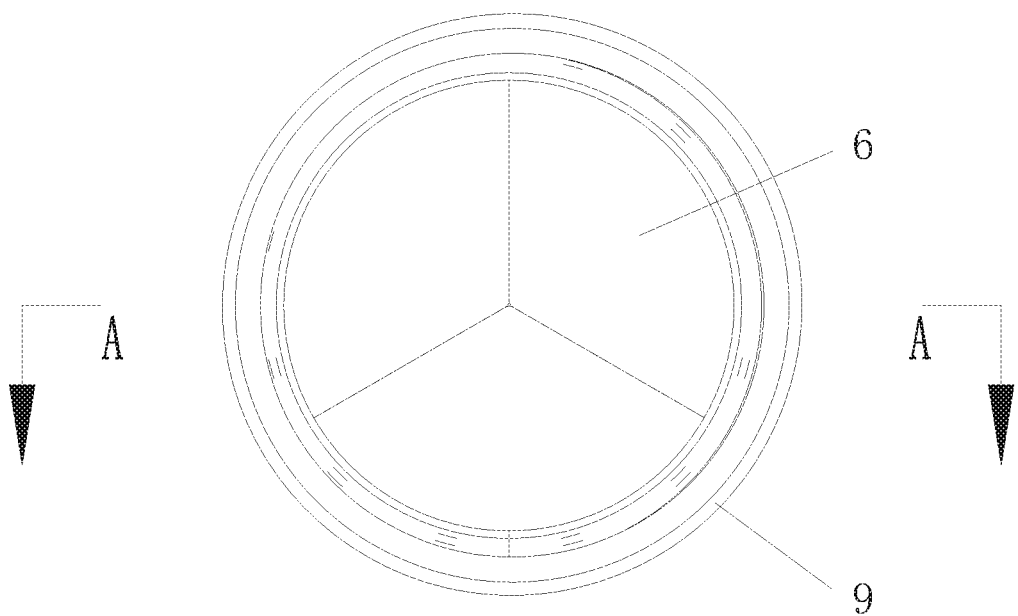
FIG. 9 is the bottom view of the prosthetic valve of the present disclosure as implanted at the pulmonary position (e.g. in pulmonary artery).
Figure 10:
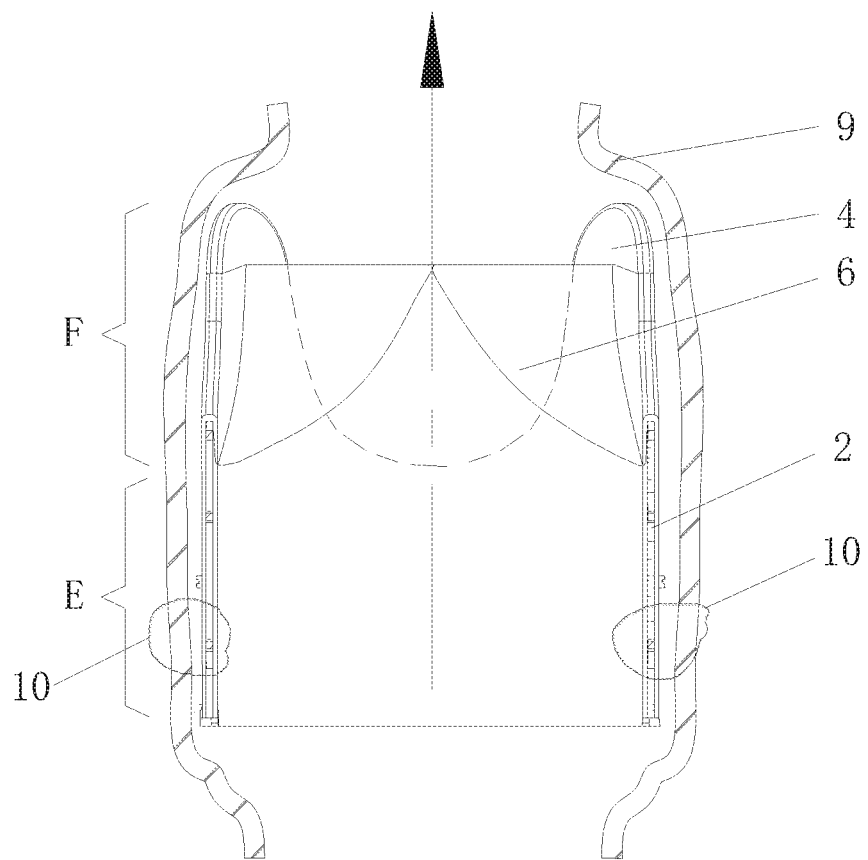
FIG. 10 is the sectional view along the line A-A of FIG. 9.

As shown in FIGS. 9 and 10, the prosthetic valve is sutured and secured to the implantation site, wherein the suturing thread 10 is sutured on the frame 2. The suturing thread 10 penetrates through the vessel wall of the implantation site and then is sutured on the frame 2. In addition, during the suturing process the suturing position may be determined by sensing such that from the exterior of the blood vessel, the special shapes of the protrusions 1 and the recessions 3 on the frame, as shown by FIG. 10, wherein the E area of the frame 2 is the part where the suturing thread 10 is sutured on, and the F area, when the prosthetic valve is in contact with the vessel wall, forms a positioning guide to determine the suturing position. The way using the suturing thread 10 is different from the suturing methods in the prior art because a horizontal suturing ring is not formed, to minimize the resistance to blood flow from the horizontal suturing ring. Thus, can prevent relatively severe destruction of protogenic valve leaflets, and has the characteristics of firm implanting and not prone to displacement and fallout, and is in particular suitable for patients for whom valve replacement surgery, such as pulmonary stenosis, is difficult.

The suturing thread 10 is sutured around the periphery of the frame 2, and the suturing forms a complete circle of sutured area (by using a continuous suture), or the suturing forms several sections of interrupted sutured areas.

Each section of the suturing thread 10 that is sutured on the vessel wall of the implantation site penetrates through the vessel wall at least twice, and the sutures are distributed in the axial direction of the frame 2, or are distributed in the circumferential direction of the frame 2.

The prior art does not provide precedents wherein a prosthetic valve is designed to be sutured on the vessel wall, so the perpendicular suturing area of the present embodiment is substantially different from the prior art.

Figure 11:
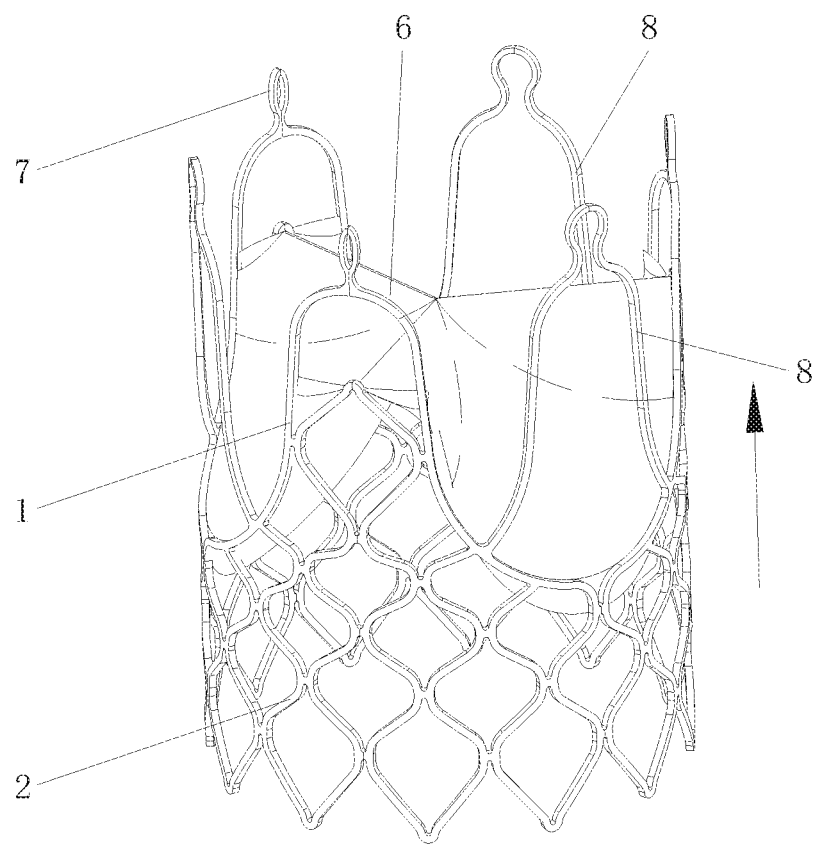
FIG. 11 shows the perspective view of the stent of the prosthetic valve of Embodiment 3 in the present disclosure (the figure also shows the valve leaflets).

In order to facilitate implantation of the prosthetic valve by transcatheter delivery, an annular guide may be provided on the arch portion of each protrusion 1. The annular guide may be connected to the retrieving element that is used in the implantation procedure, and the annular guide is formed by the bending edge at the arch portion of the protrusion 1. A sample structure is shown in FIG. 11.

The prosthetic valve is expanded for the first time during the implantation into a human body (which may also applies to other animal bodies), and the prosthetic valve is expanded after implant. The particular sizes after expanding at the implant and subsequent expansions may be adjusted according to the structures of the pulmonary artery.

Embodiment 2

Figure 2:
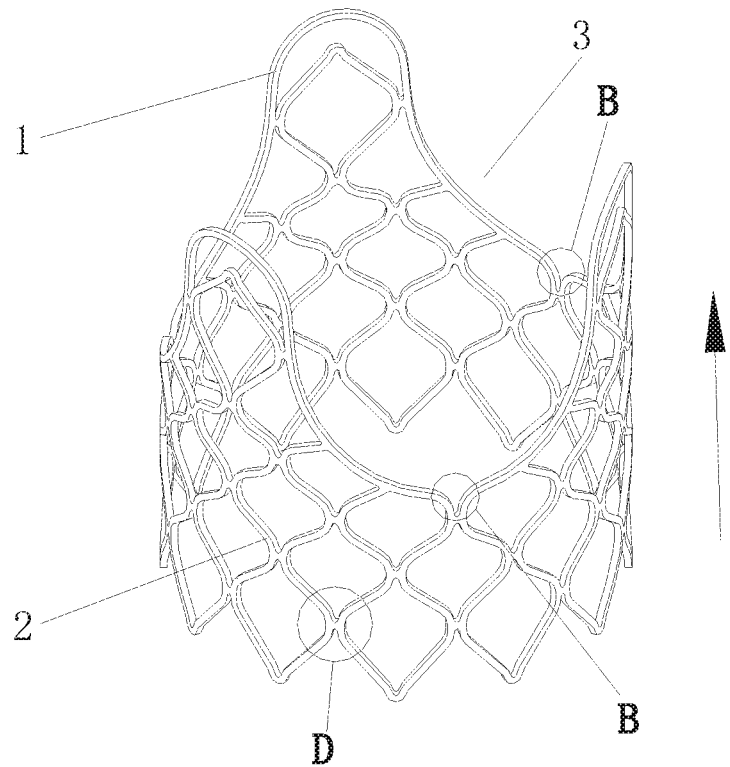
FIG. 2 is the perspective view of the stent of the prosthetic valve of Embodiment 2 in the present disclosure.

FIG. 2 shows Embodiment 2 of the present disclosure. In the present embodiment, what is different from Embodiment 1 is that all of the protrusions 1 and the recessions 3 are U-shaped, the recessions 3 comprise a combination of two smooth arcuate edges, the two arcuate edges are individually part of the protrusions 1 adjacent to the recessions, and the joint end of the two arcuate edges are connected to the lattice structure of the frame 2.

In the present embodiment, 1-3 foldable joints B are provided wherein at least 1 foldable joint 8 is provided between the bottom ends of the two smooth arcuate edges. When the prosthetic valve is expanded during implant, the foldable joints B are still in the folded state, and the foldable joints B are unfolded when the prosthetic valve is expanded after implant.

When the prosthetic valve is expanded after implant, the foldable joints B cannot be unfolded to be a smooth curve, but the foldable joints B have more integrated structure for it is part of rhombic mesh.

Optionally, the smooth arcuate edges may be individually provided with 1 foldable joint, and the foldable joints on those positions may refer to joint A in FIG. 1.

In the present embodiment, rhombic meshes are provided in the lattice structure of the frame 2. U-shaped process joints are present at intersections of the net wires, to facilitate deformation of the tubular frame when it is radially expanded, and the intersections of the net wires are of an H shape or an X shape, the H-shaped connection D is shown in FIG. 2.

The other parts of the prosthetic valve of the present embodiment are the same as those of Embodiment 1.

Embodiment 3

FIG. 11 shows Embodiment 3 of the present disclosure. In this embodiment, what is different from Embodiment 1 is that U-shaped reinforcement 8 is connected to two edges of the corresponding recession 3, the protruding direction of the reinforcements 8 is the same as the direction of the protrusions 1, and the two bottom ends of the reinforcement 8 are respectively connected to the two edges of the corresponding recession 3.

Annular guide 7 is provided on the protruding portion of each reinforcement 8, and the annular guide 7 is formed by the bending edge at the protruding portion of the reinforcement.

The annular guide 7 may be connected to the retrieving element that is used in the implantation procedure in order to adjust the implantation position of the prosthetic valve.

The frame 2, the three U-shaped protrusions 1 and the reinforcements 8 are manufactured in one process. The reinforcements 8 may also be V-shaped.

The other parts of the prosthetic valve of the present embodiment are the same as those of Embodiment 1.

Embodiment 4

Figure 12:
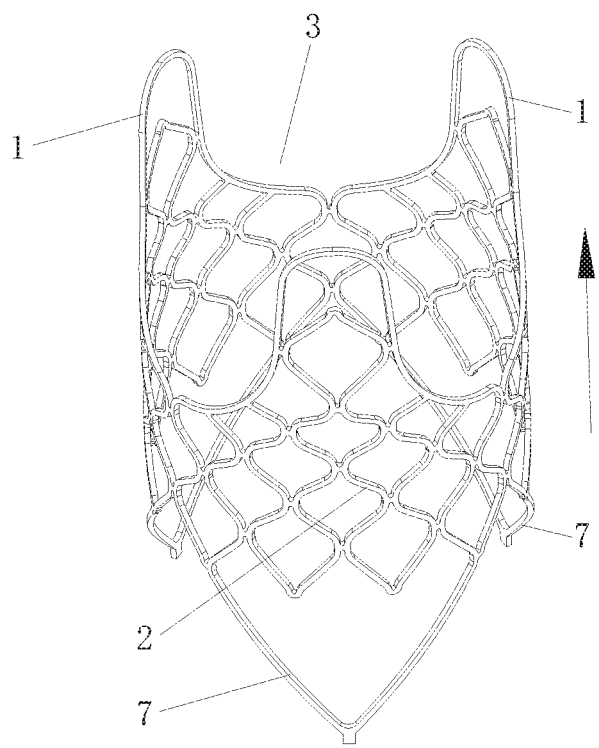
FIG. 12 shows the perspective view of the stent of the prosthetic valve of Embodiment 4 in the present disclosure.

FIG. 12 shows Embodiment 4 of the present disclosure. In this embodiment, what is different from Embodiment 1 is that several V-shaped guides 7 are provided at the upstream end of the frame 2 relative to the blood flow direction, the guides 7 extend out of the frame 2, and the guide 7 and the frame 2 are manufactured in one process.

The width of the guides 7 and the width of the net wires of the frame 2 may be the same.

The guides 7 may also be set to be U-shaped.

The guides 7 may be connected to the retrieving element that is used in the implantation procedure to adjust the implantation position of the prosthetic valve.

The other parts of the prosthetic valve of the present embodiment are the same as those of Embodiment 1.

Embodiment 5

Figure 13:
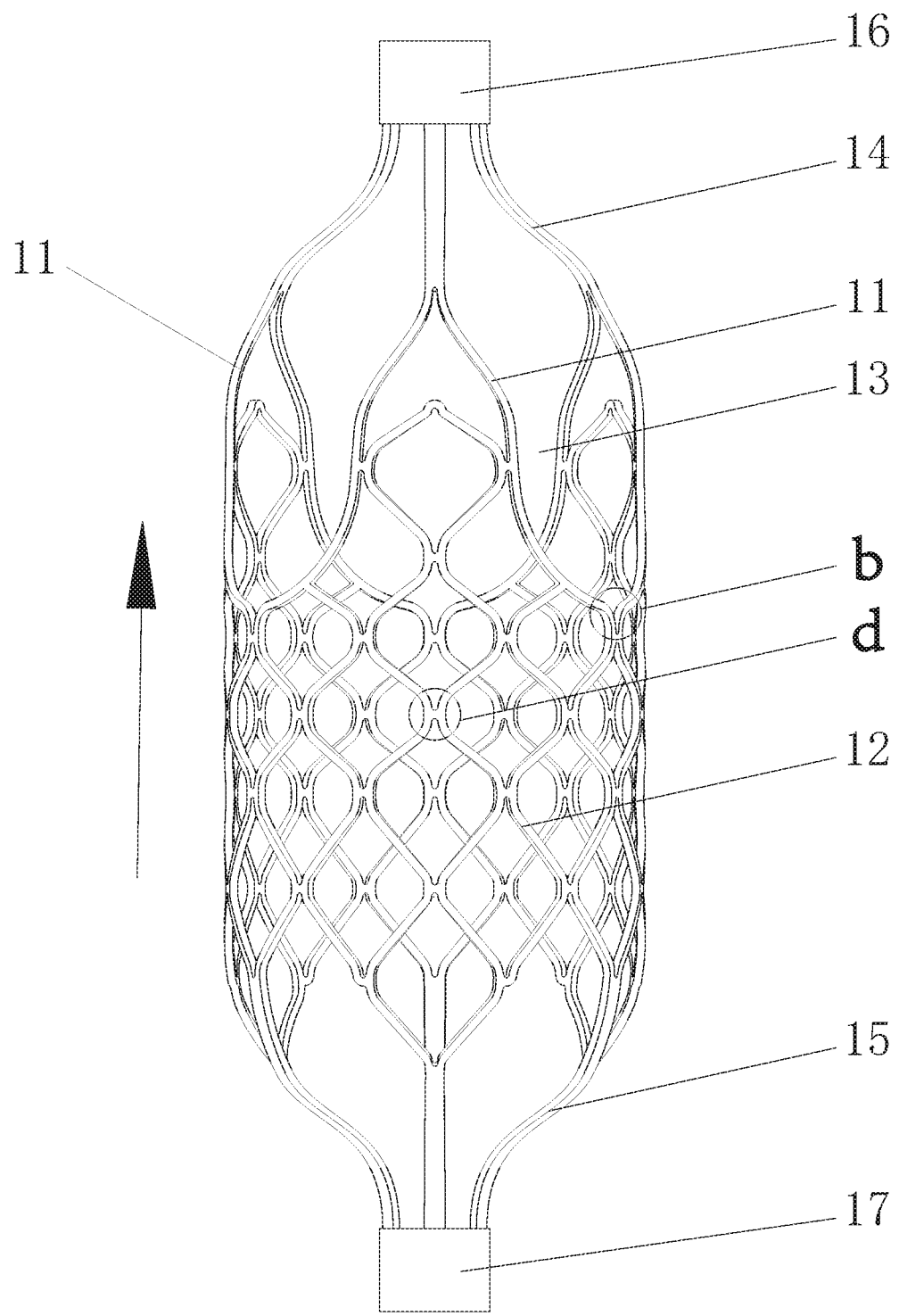
FIG. 13 shows the front view of the stent that is used as the tricuspid occluder of Embodiment 5 in the present disclosure.

FIG. 13 shows Embodiment 5 of the present disclosure. In the present embodiment, a prosthetic valve for the tricuspid position is described, which may also be referred to as tricuspid valve occluder, comprise a tubular frame 12 of a lattice structure and can be radially expanded. Three U-shaped protrusions 11 on the frame 12 are evenly arranged at the downstream end relative to the blood flow direction. A U-shaped recession 13 is provided between every two adjacent protrusions 11, several foldable joints are provided on the edges of each of the recessions 13, such as the foldable joints B shown in FIG. 13 and the foldable joints B are unfolded when the tricuspid valve occluder is expanded after implant. The top portion of the U-shaped protrusion 11 converge to a lower fixing strut 14, and three lower-fixing struts 14 are connected to a lower annular base 16.

The blood flow direction is indicated by the arrow in FIG. 13.

When the tricuspid occluder is expanded during implant, the foldable joints B are still in the folded state, or are unfolded to a small angle. In the late stage after the patient is implanted with the prosthetic valve, as the patient progresses, the tricuspid valve occluder may be balloon expanded, so as to adapt to the changing heart size of the patient.

Certainly, the recessions 13 may be provided with the structure of the foldable joints a of the first embodiment at the edges.

The frame 12 may be of a circular cylinder cage structure, or a cone cage structure, or a truncated cone cage structure.

The total length of the frame 12 may be 20-80 mm, with the internal diameter of 0.5-50 mm.

Rhombic meshes are provided within the lattice structure of the frame 12. U-shaped process slots are provided at intersections of net wires to facilitate deformation of the net wires when the tubular frame is radially expanded. The intersections of the net wires are of an H shape or an X shape, such as the H-shaped connection D shown in FIG. 13. At least three layers of the rhombic meshes are axially distributed along the frame, and the meshes extend downstream in the blood flow direction to the interior of the three U-shaped protrusions 11.

Several upper fixing struts 15 are connected to the upstream end in reference to the blood flow direction on the frame 12, and the upper fixing struts 15 are extended to an upper annular base 17. The width of the upper fixing struts 15 or the lower fixing strut 14 is greater than the width of the net wires of the frame 12.

The lower annular base 16 and the upper annular base 17 serve as the guiding elements, and can be connected to the positioning device of the prosthetic valve that is used in the implantation procedure.

The positioning device of the prosthetic valve is used for reliable positioning of the tricuspid valve occluder; which comprises a hollow sleeve that connects to an annular base and a guide wire that has an anchoring hook penetrating through the hollow sleeve and the center of the tricuspid valve occluder. The anchoring hook is located at a distal end of the guide wire and is anchored on the myocardium; the preferable anchoring position is at or near the apex of the right ventricle.

The prosthetic valve of the present embodiment may be applied in the patent for invention PCT/CN 2017/073069 "DEVICE FOR TREATING TRICUSPID REGURGITATION AND IMPLANTATION METHOD THEREOF". The patent describes a device for treating tricuspid regurgitation, and the device comprises a plug with a prosthetic valve in the tricuspid valve (abbreviated as the valve plug thereof), the valve plug can be compressed and expanded, and a fixing device for anchoring the valve plug to the tricuspid orifice. The valve plug has an inflow end and an opposite outflow end, and prosthetic valve leaflets that can open and close within the valve plug.

The covering membrane and the prosthetic valve leaflets on the frame 12 are not shown, and the configurations of those components can refer to the structure and the suturing method of the prosthetic valve of Embodiment 1 and will not be described in detail here.

The covering membrane on the frame 12 is not shown, and it can refer to the structure of the prosthetic valve of Embodiment 1, or refer to the structure of the "sleeve" in accordance with the patent PCT/CN2017/073069, and will not be described in detail here.

Embodiment 6

Figure 14:
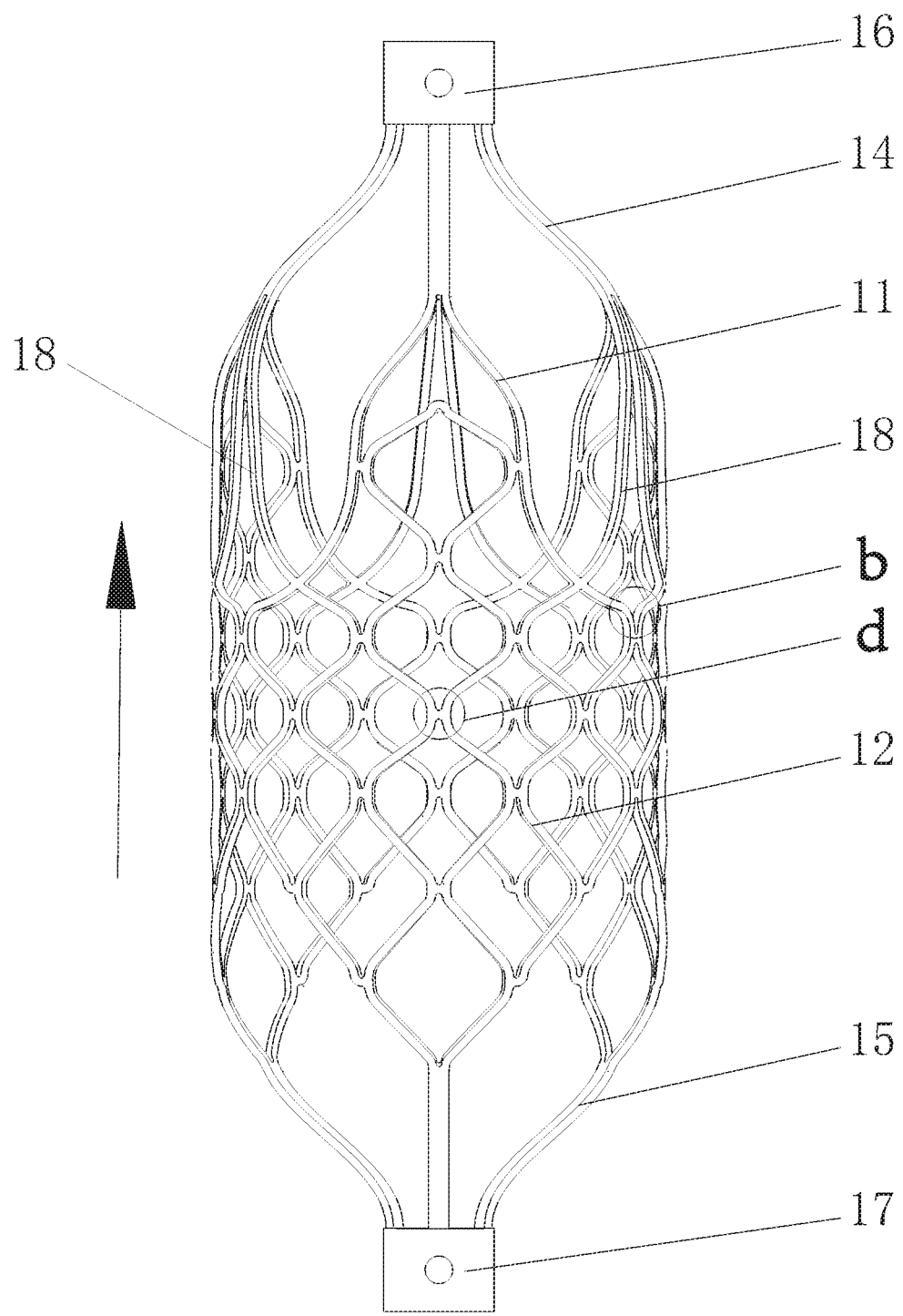
FIG. 14 shows the front view of the stent that is used as the tricuspid occluder of Embodiment 6 in the present disclosure.

FIG. 14 shows Embodiment 6 of the present disclosure. In the present embodiment, what is different from Embodiment 5 is that V-shaped reinforcement 18 is connected to two edges of the corresponding recessions 13, the protruding direction of the reinforcements 18 is the same as the protrusions 11, the two bottom ends of the reinforcement 18 are respectively connected to the two edges of the corresponding recession 13, and the protruding portion of the reinforcement 18 is connected to the lower annular base 16.

The reinforcements 18 can enhance the structural strength of the frame and facilitate withdrawal. The reinforcements 18 may also be set to be U-shaped.

The other structures of the tricuspid valve occluder of the present embodiment are the same as those of Embodiment 5 and will not be described in detail here.

The above are only the preferred embodiments of the present invention, and are not intended to limit the scope of the present invention. Any modifications, equivalents and improvements made within the spirit and scope of the present invention are included in the scope of the present invention.

What is claimed is:

1. A prosthetic valve, comprising
   a tubular frame, being of a lattice structure that can be radially expanded and distorted, wherein a plurality of U-shaped protrusions are evenly arranged on the frame configured to be placed at a downstream end relative to a blood flow direction;
   a plurality of U-shaped recession is provided between every two adjacent protrusions, one or more foldable joints are provided on edge(s) of each of the plurality of U-shaped recessions;
   wherein the protrusions and the recessions are unfolded when the prosthetic valve is expanded during implant for a first time, and the foldable joints are unfolded when the prosthetic valve is expanded for a second time after implant;
   an arch portion of each protrusion is converged to a lower fixing strut, and the lower fixing struts are connected to a lower annular base; several upper fixing struts on the frame are connected to the upstream end relative to the blood flow direction, and the upper fixing struts are connected to an upper annular base; and width of either the upper fixing struts or the lower fixing strut is greater than width of net wires of the frame.

2. The prosthetic valve according to claim 1, wherein three protrusions and three recessions are provided, three valve leaflets are attached in reference to the protrusions and the recessions, such that the valve leaflets are able to open and close in the blood flow; a covering membrane is provided on the lattice structure of the frame, and the valve leaflets are sutured on the covering membrane such that sutured portions are hermetically engaged to the covering membrane, and suturing thread is sutured through the frame or not.

3. The prosthetic valve according to claim 2, wherein the valve leaflets are sutured in reference to edges of the protrusions and the recessions, wrinkles of the valve leaflets corresponding to the foldable joints are preserved and can be expanded and stretched when the prosthetic valve is expanded after implant; and wrinkles on the covering membrane corresponding to the foldable joints are preserved and can be expanded and stretched when the prosthetic valve is expanded after implant.

4. The prosthetic valve according to claim 2, wherein the covering membrane is provided on the inner surface, or on the outer surface, or on both of the inner surface and the outer surface, of the lattice structure of the frame.

5. The prosthetic valve according to claim 4, wherein the covering membrane on the outer surface comprises an upper part and a lower part, the lower part wraps the protrusions and part of a frame body, the upper part wraps the remaining part of the frame, the upper covering and the lower covering are made of different materials or the same material, and are sutured together along a periphery of the frame.

6. The prosthetic valve according to claim 1, wherein the protrusions and the recessions are connected through a smooth curve.

7. The prosthetic valve according to claim 6, wherein 1-3 foldable joints in the shape of pointed tips are provided, and the tips of the foldable joints point up or down axially.

8. The prosthetic valve according to claim 6, wherein a U-shaped or V-shaped reinforcement is connected to two edges of a corresponding recession, the protruding direction of the reinforcements is the same as the protrusions, and the two bottom ends of each reinforcement are respectively connected to the two edges of the corresponding recession.

9. The prosthetic valve according to claim 8, wherein an annular guide is provided on the protruding portion of each reinforcement, and the annular guide is formed by bending an edge at the protruding portion of the reinforcement.

10. The prosthetic valve according to claim 1, wherein the recession comprises a combination of two smooth arcuate edges, and the arcuate edges connect smoothly to the protrusions adjacent to the recessions, and bottom ends of the arcuate edges are connected to the lattice structure of the frame.

11. The prosthetic valve according to claim 10, wherein 1-3 foldable joints are provided at each recession wherein at least 1 of the foldable joints is provided between the bottom joint of the two smooth arcuate edges, 1 foldable joint is provided on each smooth arcuate edge or not.

12. The prosthetic valve according to claim 1, wherein rhombic meshes are provided in the lattice structure of the frame, U-shaped process slots are provided at intersections of net wires, to facilitate deformation of the net wires when the tubular frame is radially expanded, and the intersections of the net wires are of a distorted H shape or an X shape.

13. The prosthetic valve according to claim 12, wherein two or more layers of the rhombic meshes are provided, and are axially distributed along the frame, and the meshes extend downwardly to interior of the protrusions in the blood flow direction.

14. The prosthetic valve according to claim 1, wherein the frame and the protrusions are manufactured by laser cutting, wire weaving or 3D printing.

15. The prosthetic valve according to claim 1, wherein the frame and the protrusions are compressed into a slim tubular shape before the prosthetic valve is radially expanded and deformed, and are expanded and deformed by a force being applied from the interior of the slim tube, or the frame and the protrusions are manufactured by using a shape memory functional material to realize self-expansion.

16. The prosthetic valve according to claim 1, wherein an annular guide is provided on an arch portion of each protrusion, and the annular guide is formed by bending an edge at the arch portion of the protrusions; or several U-shaped or V-shaped guides on the frame are provided at an upstream end relative to the blood flow direction, the guides extend out of the frame.

17. The prosthetic valve according to claim 1, wherein the upper annular base and the lower annular base form guiding elements, to connect a delivery device to position the prosthetic valve.

18. The prosthetic valve according to claim 1, wherein, a U-shaped or V-shaped reinforcement is connected to two edges of a corresponding recession, the protruding direction of the reinforcements is the same as the protrusions, and two bottom ends of each reinforcement are respectively connected to the two edges of the corresponding recession, and a protruding portion of the reinforcements is connected to the lower annular base.

19. The prosthetic valve according to claim 1, wherein the prosthetic valve is expandable during initial implant at the first time, and the prosthetic valve is expandable for further intervention after the implant at the second time after an extended use period.

\* \* \* \* \*